US009045385B2

(12) United States Patent
Julka et al.

(10) Patent No.: US 9,045,385 B2
(45) Date of Patent: *Jun. 2, 2015

(54) CONVERSION OF PROPANE TO PROPYLENE

(71) Applicant: REACTION 35, LLC, Houston, TX (US)

(72) Inventors: Vivek Julka, Fishkill, NY (US); Sagar Gadewar, Santa Barbara, CA (US); Peter K. Stoimenov, Santa Barbara, CA (US); Philip Grosso, Aubum, CA (US); Jeffrey H. Sherman, Vero Beach, FL (US); Aihua Zhang, Santa Barbara, CA (US); Eric W. McFarland, Santa Barbara, CA (US)

(73) Assignee: REACTION 35, LLC, Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,022

(22) Filed: Dec. 12, 2014

(65) Prior Publication Data

US 2015/0099911 A1   Apr. 9, 2015

Related U.S. Application Data

(63) Continuation of application No. 13/479,085, filed on May 23, 2012, now Pat. No. 8,940,954.

(60) Provisional application No. 61/489,234, filed on May 23, 2011.

(51) Int. Cl.
   *C07C 5/44*   (2006.01)
   *C07C 1/30*   (2006.01)

(52) U.S. Cl.
   CPC .............. *C07C 1/30* (2013.01); *C07C 2521/08* (2013.01); *C07C 2521/04* (2013.01); *C07C 2523/44* (2013.01)

(58) Field of Classification Search
   USPC .......... 585/324, 641; 570/241, 243, 262, 261, 570/101, 246; 95/233, 170, 159, 263
   See application file for complete search history.

(56) References Cited

U.S. PATENT DOCUMENTS 3,246,043 A * 4/1966 De Rosset et al. ............ 585/318

* cited by examiner

*Primary Examiner* — In Suk Bullock
*Assistant Examiner* — Sharon Pregler
(74) *Attorney, Agent, or Firm* — Adolph Locklar

(57) ABSTRACT

A process is disclosed that includes brominating a $C_2$, $C_3$, $C_4$, $C_5$ or $C_6$ alkane with elemental bromine to form a bromo-alkane. The bromo-alkane is reacted to form a $C_2$, $C_3$, $C_4$, $C_5$ or $C_6$ alkene and HBr. The HBr is oxidized to form elemental bromine.

19 Claims, 7 Drawing Sheets

T = 350 °C

T = 250 °C

CONVERSION OF PROPANE TO PROPYLENE

CROSS REFERENCE TO RELATED APPLICATIONS

This application is a continuation of U.S. patent application Ser. No. 13/479,085, filed on May 23, 2012, which is a Non-Provisional of U.S. Provisional Application No. 61/489,234, filed May 23, 2011 entitled "Conversion of Propane to Propylene," the entire disclosures of which are hereby incorporated by reference.

BACKGROUND

Propylene is the raw material for a variety of products including polypropylene and propylene glycol, and is traditionally produced as a by-product of steam cracking and FCC. Due to a recent shift to lighter steam cracker feedstock, which results in a lower propylene yield, and a reduced demand for motor gasoline, steam cracking may not be able to satisfy a growing demand for propylene. Consequently there is demand for increased propylene production.

BRIEF DESCRIPTION OF DRAWINGS

The present disclosure is best understood from the detailed description when read with the accompanying figures. In accordance with the standard practice in the industry, various features are not drawn to scale. Schematic drawings are structural or procedural diagrams.

DETAILED DESCRIPTION

Introduction and Definitions

Figure 1:
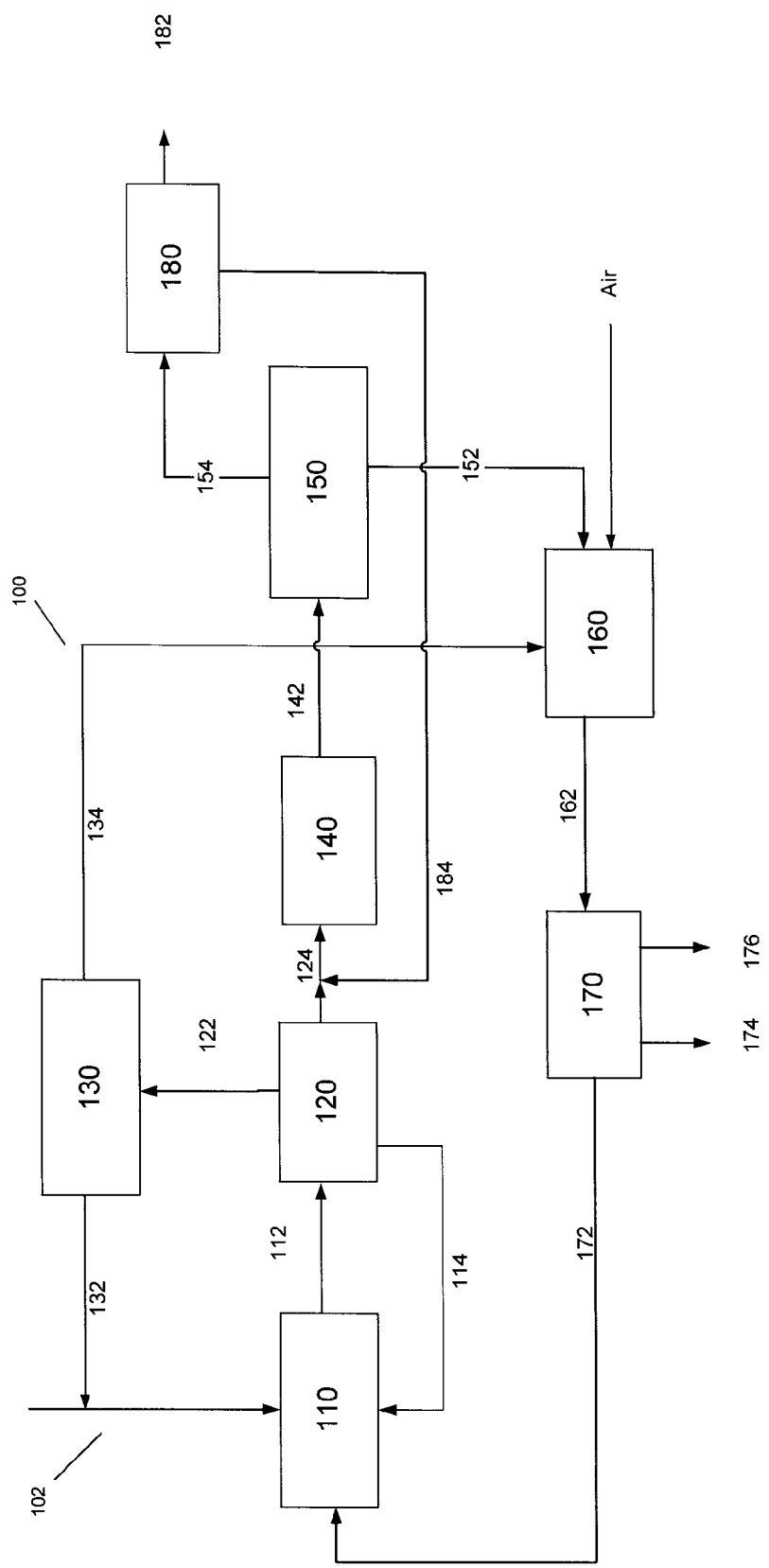
FIG. 1 is a schematic view of one embodiment of a propylene manufacturing process according to one or more aspects of the present disclosure.

The following disclosure provides many different embodiments and examples. Specific examples of equipment and arrangements are described below to simplify the present disclosure. These are merely examples and are not intended to be limiting. In addition, the present disclosure may repeat reference numerals and/or letters in the various examples. This repetition is for simplicity and clarity and does not in itself dictate a relationship between the various embodiments and/or configurations discussed.

Various terms are used herein. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Further, various ranges and/or numerical limitations may be expressly stated below. It should be recognized that any ranges include iterative ranges of like magnitude falling within the expressly stated ranges or limitations.

One non-limiting embodiment of the propylene manufacturing process of the present disclosure is shown in FIG. 1 as propylene manufacturing process 100. As shown in FIG. 1, a hydrocarbon stream that includes propane is fed to bromination reactor 110 through process feed stream 102. In addition, process feed stream 102 may include other hydrocarbons such as methane, ethane, and butane, as well as water. Water in process feed stream 102 may be at least partially removed prior to entering bromination reactor 110, such as by using one or more dryers (not shown). Butane and higher boiling hydrocarbons may be at least partially removed from process feed stream 102, such as through the use of a separation system using, for instance, distillation columns. In certain embodiments, the butane composition of process feed stream 102 entering bromination reactor 110 may be less than 600 ppm by weight of process feed stream 102.

Propane is reacted with elemental bromine in bromination reactor 110 to produce bromopropane and HBr. In certain embodiments of the present disclosure, this reaction is not catalyzed, i.e., the reaction is only thermally induced. Thermal induction means bringing the reactants to an initiation temperature. In other embodiments, the reaction may be catalyzed. In addition to bromopropane and HBr, the reaction may form byproducts dibromopropane, propyl polybromides, propylene, and other alkyl bromides. At higher temperatures, coke may also be formed in bromination reactor 110.

Figure 2A:
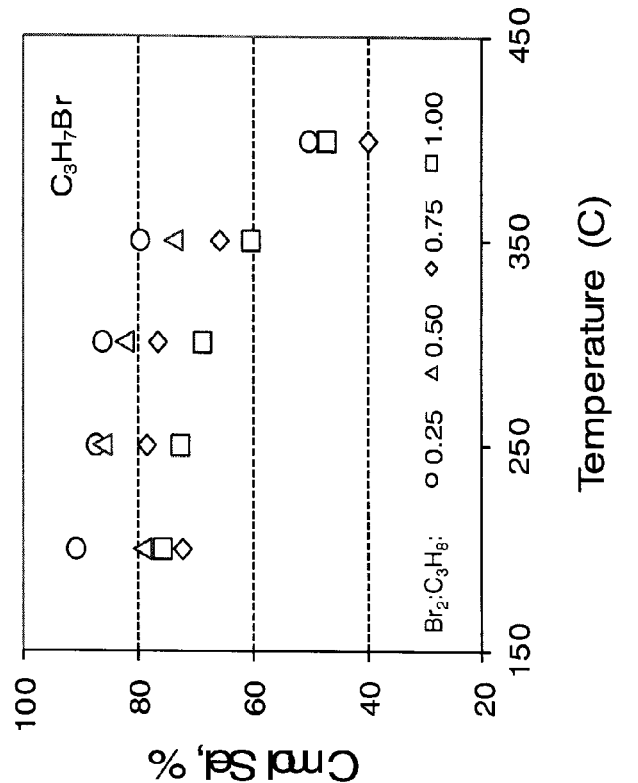
FIG. 2A is a graph of conversion of propane as a function of temperature for several bromine to propane ratios.
Figure 2B:
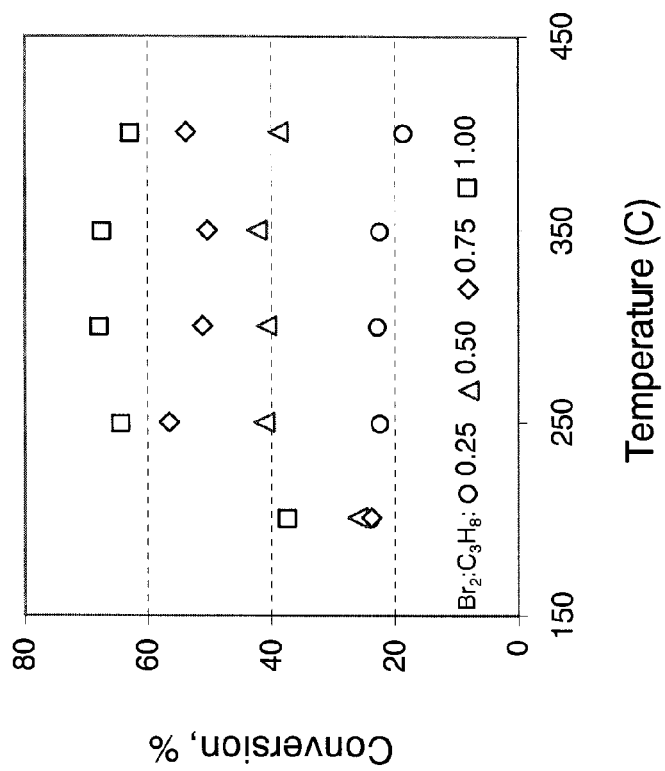
FIG. 2B is a graph of selectivity for $C_3H_7Br$ as a function of temperature for several bromine to propane ratios.
Figure 3B:
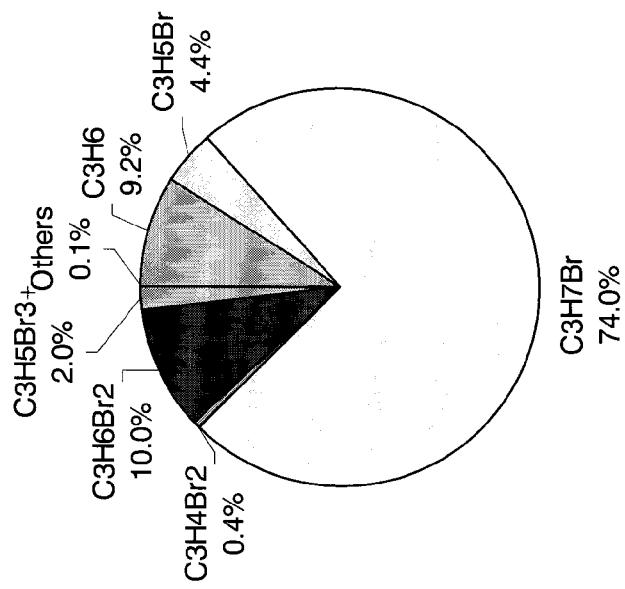
FIG. 3B is a graph for the selectivity at 350° C. for a bromine to propane ratio of 0.50 at a residence time of 30 seconds.
Figure 3A:
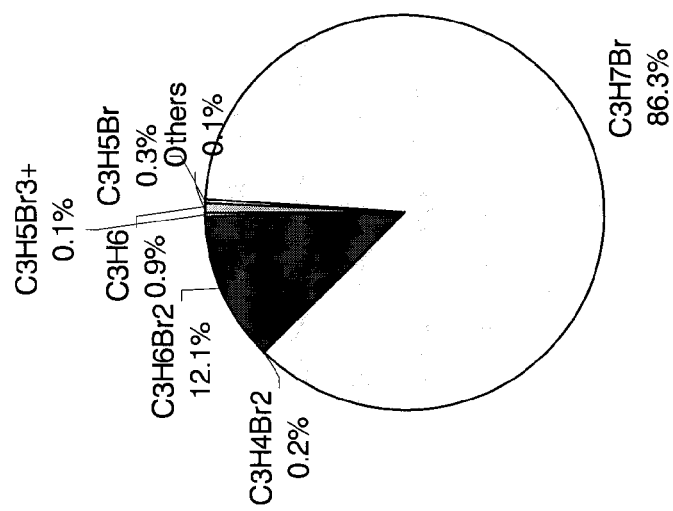
FIG. 3A is a graph for the selectivity at 250° C. for a bromine to propane ratio of 0.50 at a residence time of 30 seconds.

FIG. 2A shows the conversion of propane to products as a function of temperature for bromine to propane ratios of 0.25, 0.50, 0.75 and 1.00 for a residence time of 30 seconds. FIG. 2B shows the selectivity of the reaction of propane to bromopropane as a function of temperature at bromine to propane ratios of 0.25, 0.50, 0.75 and 1.00 for a residence time of 30 seconds. FIGS. 3A and 3B show the selectivity at 250° C. and 350° C. respectively for a bromine to propane ratio of 0.50 at a residence time of 30 seconds. One of skill in the art with the benefit of this disclosure will recognize that conversion and selectivity can be controlled by varying the temperature in bromination reactor 110, with higher temperatures tending to increase the conversion of propane and elemental bromine to products, but also to decrease selectivity to bromopropane and increased production of coke. In certain embodiments, increasing the bromine to propane ratio may decrease the selectivity of propane to bromopropane.

The bromination reaction occurs at temperatures above 200° C. Above 450° C., the bromination reaction may produce unacceptable levels of coke. In certain embodiments of the present disclosure, the bromination reaction may occur between 200° C. and 450° C. In certain embodiments of the present disclosure, the temperature in bromination reactor 110 is between 200° C. to 375° C. In certain embodiments, this temperature range may be used for propane, butane and pentane.

In certain other embodiments of the present disclosure, the outlet temperature of the stream leaving the bromination reactor 110 may be between 250° C. and 350° C. to achieve a desired conversion of bromine. The desired level of conversion of bromine may be greater than 99%. In addition, propylene may also be recycled from product separation section 180 to the outlet of bromination reactor 110 to achieve this desired level of conversion of bromine (not shown). A more complete conversion of bromine in bromination reactor 110 may allow for the use of less expensive materials of construction downstream of bromination reactor 110.

Because the reaction of propane with elemental bromine is exothermic, bromination reactor 110 may be cooled to maintain the bromination reaction within the desired temperature range. In certain embodiments, bromination is carried out in a shell and tube reactor, in which a mixed propane and bromine feed is introduced into the bromination reactor at a temperature greater than or equal to 200° C. The bromination reaction may be carried out inside the tubes, and steam may then be generated on the shell side in order to limit the maximum temperature of the bromination reaction to the desired temperature range, such as 250° C.-350° C. The generated steam may be used elsewhere in the process.

In certain embodiments of the present disclosure, a stoichiometric excess of propane may be used to increase selectivity to bromopropane and/or to limit temperature rise. In other embodiments of the present disclosure, bromination is carried out in one or more adiabatic reactors with cooling between the different reactors. This cooling may be achieved using heat exchanger(s) or cold (~35° C.) bromine or propane. In certain other embodiments of this disclosure, cold (~35° C.) bromine is introduced at multiple positions along the length of the bromination reactor in order to keep the reaction temperature within the desired range. In certain embodiments, this reaction is carried out at higher than atmospheric pressure. In certain other embodiments, this pressure is near that required for subsequent downstream separations. This may significantly improve the efficiency of the entire process by reducing, or preferably eliminating, any required downstream compression prior to separation Products and byproducts of the bromination reaction, along with any excess propane, are discharged from bromination reactor 110 through bromination discharge stream 112, which feeds distillation section 120. In certain embodiments of the present disclosure, distillation section 120 includes one or more distillation columns that separate the compounds of bromination discharge stream 112 into lights stream 122, bromopropane stream 124 and recycle stream 114. In the embodiment shown in FIG. 1, bromopropane stream 124 is predominantly bromopropane. In some embodiments, the amount of bromopropane and bromopropylene in bromopropane stream 124 may exceed 99%. The lights stream 122 may be predominantly propane and HBr, but may also contain methane, ethane, butanes, light hydrocarbons and light gases. Bromination recycle stream 114 includes dibromopropane, propane polybromides and other alkyl bromides.

In the embodiment shown in FIG. 1, lights stream 122 is further separated using absorption-stripping process 130. In absorption-stripping process 130, the HBr in lights stream 122 is absorbed. In certain embodiments of the present disclosure, the HBr is absorbed using aqueous HBr. This aqueous HBr may be kept chilled, such as around approximately 45° C. Any remaining HBr in the propane may be subsequently absorbed using an absorption agent such as water to yield a substantially HBr-free propane gas stream. The HBr absorption process is highly exothermic. In certain embodiments, the absorber may be cooled by conventional methods. In one embodiment, the absorber uses a pump-around cooling system to remove the heat of absorption. In the embodiments shown in FIG. 1, after absorption, the concentrated aqueous HBr may be sent to a stripper that is part of absorption-stripping process 130 where relatively dry HBr gas is stripped from the aqueous HBr. In certain embodiments the water content of the dry HBr gas is approximately 2 wt %. Non-limiting examples of the absorption/stripping process may be found in U.S. application Ser. No. 12/504,880, filed Jul. 17, 2009, incorporated fully herein by reference. The hot dilute aqueous HBr stream leaving the stripper is cooled and recycled to the absorber.

After absorption of the HBr, the remaining propane may be compressed and discharged from absorption stripping process 130 through recycle propane stream 132. In the embodiment shown in FIG. 1, recycle propane stream 132 is combined with process feed stream 102. The dry HBr gas is removed from absorption stripping process 130 through HBr gas stream 134.

The dibromopropane of recycle stream 114 may be subsequently reacted, thermally or in the presence of a catalyst, with propane to form bromopropane. In certain embodiments, the propane polybromides and other alkyl bromides react with propane to form bromopropane. In the embodiment shown in FIG. 1, bromination recycle stream 114 is recycled to bromination reactor 110 where the reaction with propane is thermal and may occur simultaneously with propane bromination. In another embodiment, the reaction of dibromopropane, and, if desired, other propane polybromides with propane to form bromopropane occurs in a separate reactor from bromination reactor 110. In still another embodiment (not shown), the dibromopropane and other alkyl polypolybromides may be either partially hydrogenated to bromopropane and/or to completely hydrogenate to propane (and other corresponding alkanes) using $H_2$ in the presence of a catalyst such as Pd, Pt, Ni, Ru, Rh, and Cu. In this embodiment, the reaction may be carried out in the presence of HBr to improve the selectivity to bromopropane and minimize coke formation. HBr formed in this reaction may be recovered and sent to the oxidation section (discussed below), while the bromopropane and the alkanes may be recycled to distillation section 120. In still yet another embodiment, the dibromopropane is converted directly to propylene using Zn which produces $ZnBr_2$ as a byproduct. $ZnBr_2$ may then be used to regenerate $Br_2$ using oxidation or electrolysis. This treatment using Zn may also be used as a cleanup step to remove small amounts of dibromopropane and other propane polybromides from process streams.

Figure 4:
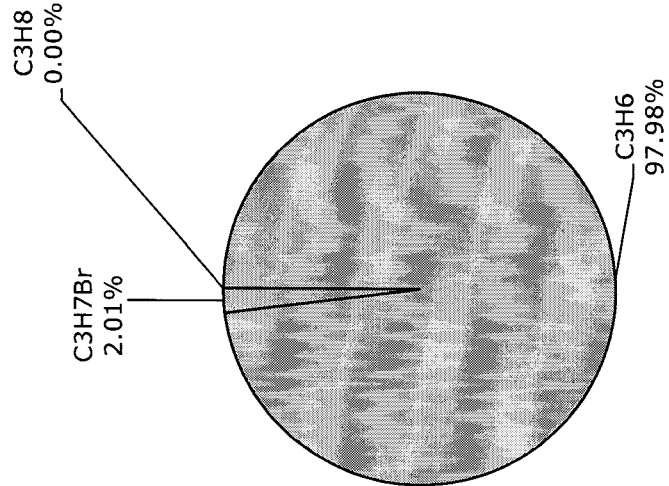
FIG. 4 is a graph of the product distribution of dehydrobromination of 2-bromopropane to propylene using WR Grace Silica 1151.
Figure 5:
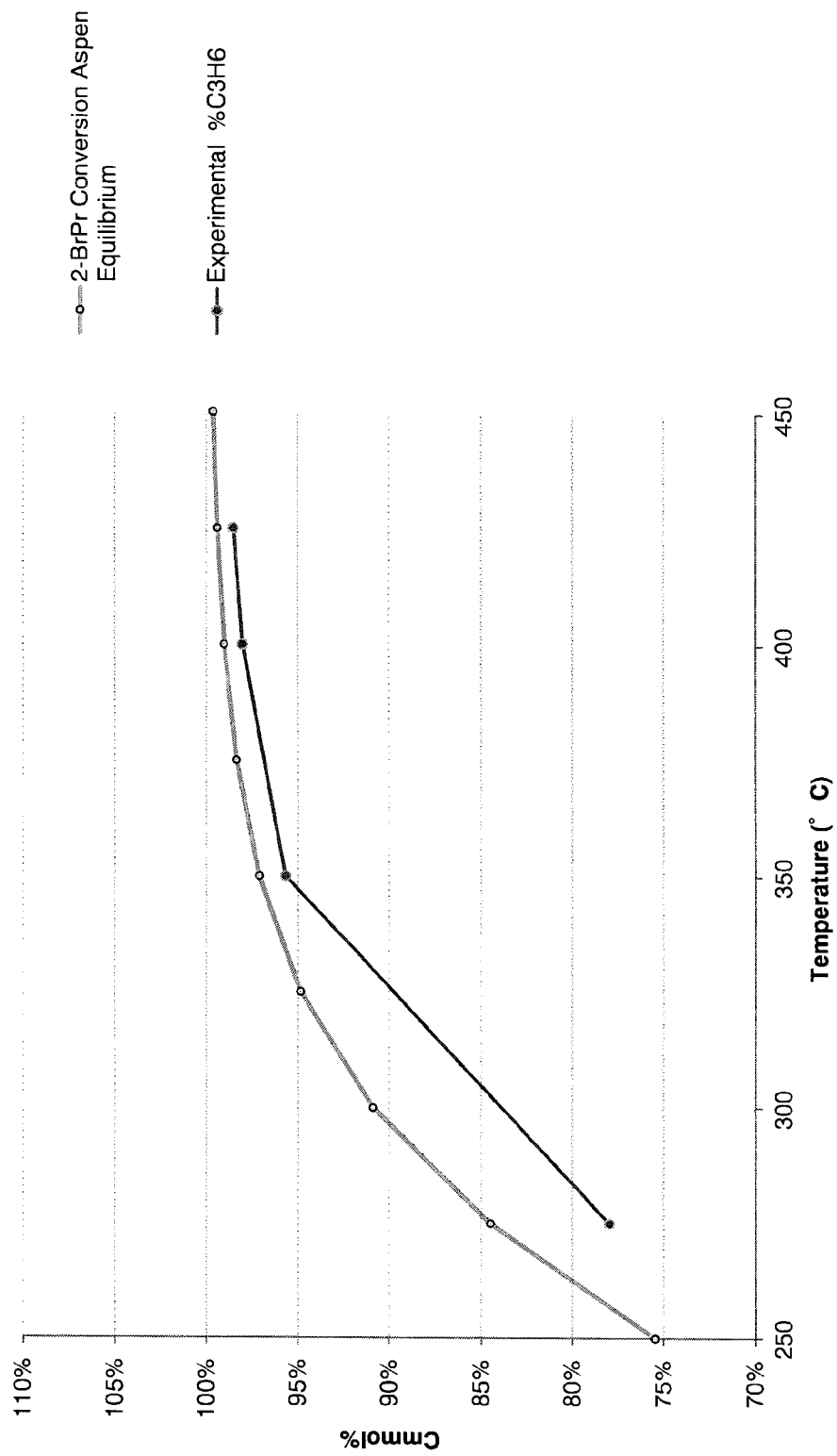
FIG. 5 is a graph comparing bromopropane conversion at equilibrium with experimental results.

With further reference to FIG. 1, bromopropane stream 124 is optionally heated (not shown) and fed to dehydrobromination reactor 140 to form propylene and HBr. In certain embodiments of the present disclosure, this reaction is performed thermally, i.e., non-catalytically. However, in certain circumstance, a thermal reaction in dehydrobromination reactor 140 may be slow. Such slow reaction rate may require long residence times and/or high temperature in order to achieve suitable conversion. In an alternative embodiment, the reaction in dehydrobromination reactor 140 may be carried out in the presence of a catalyst, such as a silica-based catalyst. One example of a suitable silica catalyst is WR Grace Silica 1151. As shown in FIGS. 5 and 4 respectively, Si 1151 exhibits conversion of bromopropane close to thermodynamic equilibrium and has a selectivity of greater than 99% with residence times less than 1 second. In order to shift the equilibrium in the desired direction, in certain embodiments, the reaction is carried out at a temperature of 250° C.-500° C.

In certain embodiments, this reaction is carried out at higher than atmospheric pressure. In certain other embodiments, this pressure is near that required for subsequent downstream separations. This significantly improves the efficiency of the entire process by reducing, or preferably eliminating, any required downstream compression prior to separation.

Dehydrobromination reactor discharge stream 142 contains propylene, HBr and unconverted bromopropane. In the embodiment shown in FIG. 1, dehydrobromination reactor discharge stream 142 is fed to HBr absorption section 150. In HBr absorption section 150, the HBr in dehydrobromination reactor discharge stream 142 is absorbed. In certain embodiments of the present disclosure, the HBr is absorbed using aqueous HBr. This aqueous HBr may be kept chilled, such as around approximately 45° C. Any remaining HBr in the propylene and unconverted bromopropane may be subsequently absorbed using an absorption agent such as water to yield a substantially HBr-free propylene/bromopropane stream. The HBr absorption process is highly exothermic. In certain embodiments, the absorber may be cooled by conventional methods. In one embodiment, the absorber uses a pump-around cooling system to remove the heat of absorption. In the embodiments shown in FIG. 1, after absorption, any bromopropane and/or propylene present in the concentrated aqueous HBr stream leaving the absorber are recovered using liquid-liquid phase separation and/or distillation. A mass-separating agent may be used to facilitate the separation. The concentrated aqueous HBr is sent to a stripper that is part of HBr absorption section 150 where relatively dry HBr gas is stripped from the aqueous HBr. In certain embodiments the water content of the dry HBr gas is approximately 2 wt %. The hot dilute aqueous HBr stream leaving the stripper is sent to HBr oxidation unit 160 in oxidation feed stream 152. The bromopropane and propylene leaving HBr absorption section 150 is sent to product separation unit 180 through product separation feed stream 154.

In product separation unit 180, the bromopropane in product separation feed stream 154 is separated from the propylene. In certain embodiments, the propylene may undergo a final water wash and a drying step in product separation unit 180. Propylene exits product separation unit 180 through product line 182. The propylene in product line 182 may be high-purity propylene product, such as polymer grade propylene. Recycle bromopropane stream 184 may be combined with bromopropane stream 124 and recycled to dehydrobromination reactor 140.

A thermodynamic analysis of the bromopropane dehydrobromination reaction shows that while bromopropane dehydrobromination is favored at high temperatures, the hydrobromination of propylene by HBr is favored at lower temperatures. Certain non-limiting embodiments for minimizing propylene hydrobromination in the HBr absorption section 150 include:

1) Dehydrobromination reactor discharge stream 142 may be mixed with cold (gaseous and/or liquid) propylene, preferably at a temperature between 10° C. and 80° C. and/or cold liquid bromopropane, preferably at a temperature between 10° C. and 80° C. to significantly reduce, or suppress, propylene hydrobromination in product separation unit 170. In order to promote rapid mixing and cooling, the streams may be mixed in certain embodiments using, for instance a venturi, or spray tower, or in dehydrobromination reactor 140 itself.

2) Dehydrobromination reactor discharge stream 142 may be contacted with cold (e.g., approximately 45° C.) aqueous HBr in an absorber to selectively absorb the HBr while simultaneously suppressing or significantly reducing propylene hydrobromination.

3) The hot stream leaving dehydrobromination reactor 140 may be rapidly cooled using one or more heat exchangers to minimize any hydrobromination of propylene. This alternative embodiment may also maximize energy recovery from this stream, which may be used elsewhere in the process or outside the process.

In the embodiment shown in FIG. 1, oxidation feed stream 152 is mixed with oxygen, for instance through the introduction of an air stream. The HBr gas may then be oxidized over a catalyst, such as a chromium or cerium oxide-based catalyst to produce bromine and water. The initiation temperature for this catalytic reaction is approximately 200° C., while the maximum stable operating temperature for the catalyst is approximately 700° C. HBr oxidation is a highly exothermic reaction and may be carried out using a reactor system, such as an isothermal reactor or a multiple stage adiabatic reactor system with intermediate cooling using quench and/or heat exchangers. Examples of such systems may be found in U.S. Pat. No. 7,883,568, issued Feb. 8, 2011, which is incorporated fully herein by reference.

In the embodiment shown in FIG. 1, oxidation reactor exit stream 162 is fed to bromine separator 170. In bromine separator 170, the bromine in oxidation reactor exist stream 162 may be subsequently condensed, and bromine and water (which are substantially immiscible) are separated, such as by using a decanter. Elemental bromine from bromine separator 170 may be recycled to bromination reactor 110 through bromine recycle stream 172, while water and a gas stream (primarily including nitrogen and oxygen) may be discharged through water discharge stream 174 and gas discharge stream 176, respectively.

While the bulk of the bromine may be recovered by condensation in bromine separator 170, the gas stream, consisting primarily of nitrogen and the excess oxygen when air is used as the oxidizing stream, leaving the oxidation system may still contain a small amount of bromine. Cold (e.g., ~45° C.) aqueous sodium bromide may be used to recover the residual bromine using a reactive absorption process. The absorbed bromine may then be recovered using heterogeneous distillation, and the lean aqueous sodium bromide solution may be cooled and recycled to the absorber.

Figure 1A:
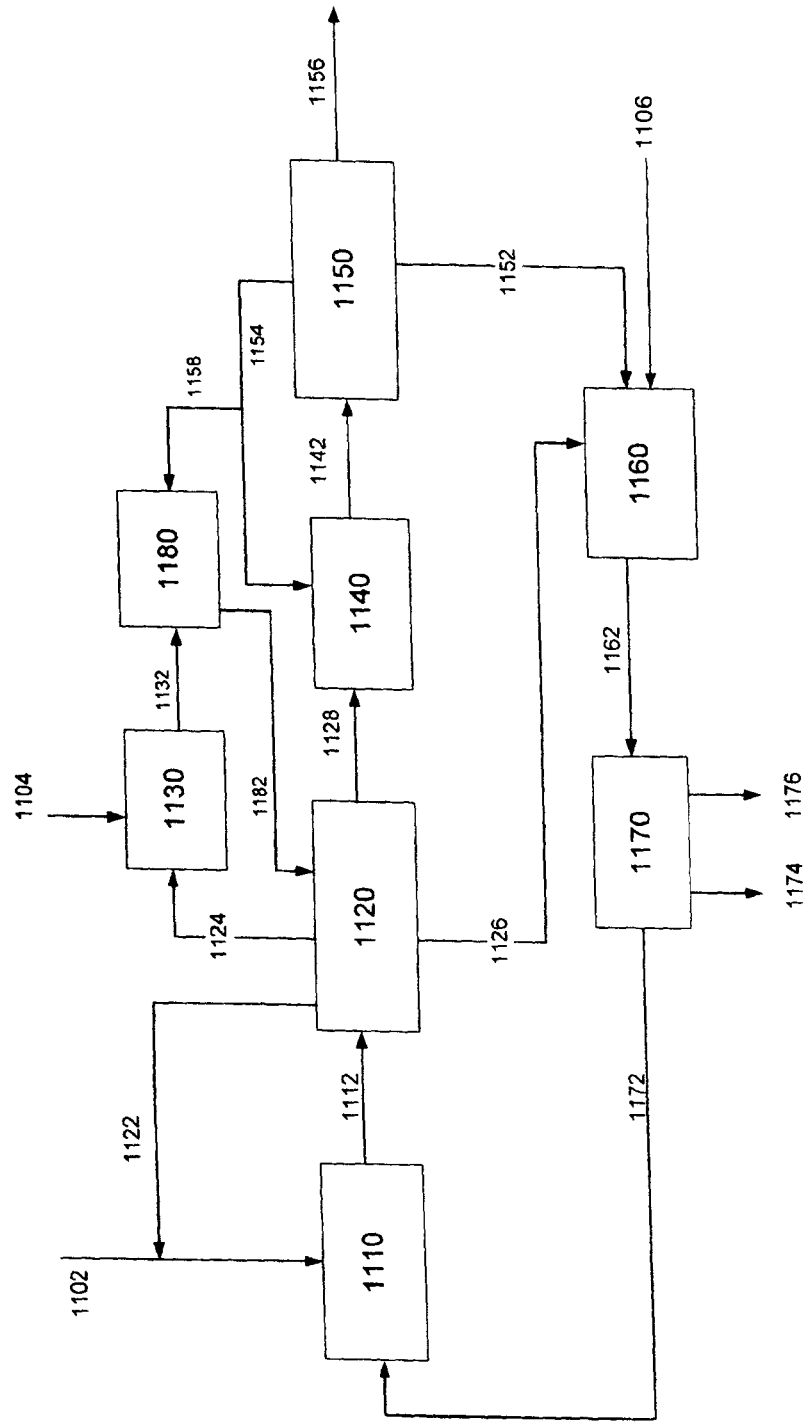
FIG. 1A is a schematic view of another embodiment of a propylene manufacturing process according to one or more aspects of the present disclosure.

FIG. 1A is a schematic view of another embodiment of a propylene manufacturing process according to one or more aspects of the present disclosure shown as propylene manufacturing process 1000. In this embodiment, a hydrocarbon stream containing predominantly propane is fed to bromination reactor 1110 through process feed stream 1102. In addition to propane, the feed stream may also contain small amounts of other hydrocarbons, including methane, ethane, and butane, and water. Water in the process feed stream 1102 may be at least partially removed prior to entering bromination reactor 1110, such as by using one or more dryers (not shown). Butane and higher boiling hydrocarbons may also be at least partially removed from process feed stream 1102, such as through the use of one or more distillation columns. In certain embodiments, the butane composition of process feed stream 1102 entering bromination reactor 1110 may be less than 600 ppm by weight of process feed stream 1102.

Propane is reacted with elemental bromine in bromination reactor 1110 to produce bromopropane and HBr. In certain embodiments of the present disclosure, this reaction is not catalyzed, i.e., the reaction is thermally induced. Thermal induction means bringing the reactants to an initiation temperature. In addition to bromopropane and HBr, the reaction may form byproducts dibromopropane, propyl polybromides, propylene, bromopropylene, and other alkyl bromides. The bromination reaction occurs at temperatures above 200° C. Propane conversion and selectivity to bromopropane can be controlled by varying the temperature and the propane to bromine ratio, as shown in FIGS. 2A and 2B. Higher reaction temperatures tend to increase the conversion of propane and elemental bromine to products, but also to decrease selectivity to bromopropane and increased production of coke. In certain embodiments of the present disclosure, the temperature of the bromination reaction is between 200° C. to 450° C. In certain other embodiments of the present disclosure, the temperature of the bromination reaction is between 200° C. and 375° C. In certain other embodiments of the present disclosure, the temperature of the stream leaving the bromination reactor 1110 is between 250° C. and 350° C. to allow a more complete (>99%) conversion of bromine. In addition, propylene may also be recycled from the product separation section 1150 to the outlet of bromination reactor 1110 to allow a more complete (>99%) conversion of bromine (not shown). A more complete conversion of bromine in the bromination reactor allows for the use of less expensive materials of construction downstream of the bromination reactor.

Because the reaction of propane with elemental bromine is exothermic, bromination reactor 1110 may be cooled to maintain bromination reactor 1110 within the desired temperature range. In certain embodiments, bromination is carried out in a shell and tube reactor, in which a mixed propane and bromine feed is introduced into the bromination reactor at a temperature greater than or equal to 200° C., the bromination reaction is carried out inside the tubes, and steam is generated on the shell side in order to limit the maximum temperature of the bromination reaction to 250° C.-350° C. Alternatively, the shell-and-tube reactor may be configured to carry out the reaction on the shell side with steam generation within the tubes. The generated steam may be used elsewhere in the process.

In certain embodiments of the present disclosure, a stoichiometric excess of propane may be used to increase selectivity to bromopropane and/or to limit temperature rise. In other embodiments of the present disclosure, bromination is carried out in one or more adiabatic reactors with cooling between reactors connected in series. This cooling may be achieved using heat exchanger(s) or direct injection of cold (~35° C.) bromine or propane. In certain other embodiments of this disclosure, cold (~35° C.) bromine is introduced at multiple positions along the length of the bromination reactor in order to keep the reaction temperature within the desired range. In certain embodiments, this reaction is carried out at higher than atmospheric pressure. In certain other embodiments, this pressure is near that required for subsequent downstream separations. This may significantly improve the efficiency of the entire process by reducing, or preferably eliminating, any required downstream compression prior to separation.

Products and byproducts of the bromination reaction, along with any excess propane, are discharged from bromination reactor 1110 through bromination discharge stream 1112, which feeds bromopropane recovery section 1120. In certain embodiments of the present disclosure, bromopropane recovery section 1120 includes one or more distillation columns that separate the compounds of bromination discharge stream 1112 into propane recycle stream 1122, HBr stream 1126, dibromopropane stream 1124 and bromopropane stream 1128. Propane recycle stream 1122 is predominantly propane, and may also contain small amounts of propylene, HBr, bromopropane, butanes and other hydrocarbons, and is recycled to bromination reactor 1110 where it is reacted with elemental bromine. HBr stream 1126 is predominantly HBr, with possibly some methane, ethane, light gases (e.g., $H_2$, $N_2$, $O_2$, etc.) propane and propylene. Dibromopropane stream 1124 contains species with a boiling point significantly greater (>10° C.) that that of bromopropane at the distillation column operating conditions, and includes dibromopropane, propyl polybromides and other alkyl bromides. Bromopropane stream 1128 is predominantly bromopropane, with small amounts of bromopropylene, propane and dibromopropane. In some embodiments, the amount of bromopropane and bromopropylene combined in bromopropane stream 1128 is at least 99 wt %. In some embodiments, distillation is carried out at a pressure high enough to allow for the use of cooling water in the condensers.

Dibromopropane stream 1124 feeds hydrogenation section 1130, where it is reacted with $H_2$ stream 1104 in the presence of a catalyst such as Pd, Pt, Ni, Ru, and Cu, to yield primarily bromopropane and HBr, along with some bromopropylene, propane, alkyl bromides and other hydrocarbons. In certain embodiments this reaction may be carried out in the presence of HBr, which may be recycled from stream 1126 (not shown), to improve the selectivity to bromopropane and minimize coke formation. Because hydrobromination is an exothermic reaction, in a certain embodiment, the reaction is carried out in a reactor with heat removal capabilities. In another embodiment, hydrogenation 1130 is a multistage adiabatic reactor, with one or stages and inter-stage cooling.

Hydrogenation reactor effluent 1132 is subsequently mixed with stream 1158, and fed to hydrobromination 1180, where bromopropylene reacts with HBr, in the presence of a catalyst, to form dibromopropane. One such catalyst is WR Grace Silica 1151. The maximum extent of the conversion of bromopropylene to dibromopropane is determined by equilibrium. In some embodiments, some HBr from the bromopropane recovery system is optionally (not shown) recycled to hydrobromination 1180, in order to increase the conversion of bromopropylene to dibromopropane. In a certain embodiment, hydrobromination 1180 is an adiabatic reactor. In certain embodiments, the reaction is carried out at higher than atmospheric pressure in order to maximize the selective hydrogenation of dibromopropane and the conversion of bromopropylene to dibromopropane. Hydrobromination reactor discharge stream 1182 is recycled to the bromopropane recovery section 1120.

With further reference to FIG. 1A, bromopropane stream 1128 may be heated and fed to dehydrobromination reactor 1140 to form propylene and HBr. In certain embodiments of the present disclosure, this reaction is performed thermally, i.e., non-catalytically. However, in certain circumstance, a thermal reaction in dehydrobromination reactor 1140 may be slow. Such slow reaction rate may require long residence times and/or high temperature in order to achieve suitable conversion. In an alternative embodiment, the reaction in dehydrobromination reactor 1140 may be carried out in the presence of a catalyst. Examples of such catalysts include a silica based catalysts, for example, WR Grace Silica 1151 or other materials with highly polar surfaces such as silicalite (aluminum free silica with ZSM-5 or ZSM-11 like crystal structure), silica gel, precipitated silica, mesoporous silica (such as Sigma-Aldrich sourced HMS silica), fumed silica (such as that sourced by Cabot Corp.), titanium dioxide (rutile and anatase), zirconium dioxide and their mixtures thereof and other single or mixed metal oxides. As shown in FIGS. 4 and 5, the WR Grace Silica 1151 catalyst exhibits conversion of bromopropane close to thermodynamic equilibrium and has a selectivity of greater than 99% with residence times less than 1 second. Dehydrobromination of bromopropane to propylene and HBr is an equilibrium reaction, and in order to shift the equilibrium in favor of propylene formation, in certain embodiments, the reaction is carried out at a temperature of 250° C.-500° C. In certain embodiments, this reaction is carried out at higher than atmospheric pressure. In certain other embodiments, this pressure is near that required for subsequent downstream separations. This significantly improves the efficiency of the entire process by reducing, or preferably eliminating, any required downstream compression prior to separation.

Because bromopropane dehydrobromination is an endothermic reaction, in a certain embodiment, heat is added to dehydrobromination reactor 1140 so as to maintain the reaction within the desired temperature levels. The heat may be provided using hot flue gas, a flame, hot oil, molten salt, electricity, high pressure steam, or other suitable heat source, depending on the desired dehydrobromination reaction temperature. In another embodiment, dehydrobromination is carried out in a multistage adiabatic reactor, with interstage heating. In a certain other embodiment, dehydrobromination is carried out partially in a reactor with heat added, and partially in an adiabatic reactor. In yet another embodiment, the dehydrobromination reactor 1140 may be configured so that the dehydrobromination reaction occurs partially thermal and partially catalytic.

Dehydrobromination reactor discharge stream 1142 contains propylene, HBr, unconverted bromopropane and bromopropylene, and is fed to the product recovery 1150. A thermodynamic analysis of the bromopropane dehydrobromination reaction shows that while bromopropane dehydrobromination is favored at high temperatures, the hydrobromination of propylene by HBr is favored at lower temperatures. In order to minimize propylene hydrobromination in the product separation section 1150, in certain embodiments, dehydrobromination reactor discharge stream 1142 is rapidly cooled using one or more heat exchangers. This embodiment may also maximize energy recovery from this stream, which may be used elsewhere in the process or outside the process. In another embodiment, the dehydrobromination reactor discharge stream 1142 may be quenched by mixing it with cold (gaseous and/or liquid) propylene and/or cold liquid bromopropane from the product separation section 1150 to significantly reduce, or suppress, propylene hydrobromination. In certain embodiments, the temperature of the propylene and/or bromopropane stream is 10° C.-80° C., in order to maximize cooling without the need for refrigeration. In order to promote rapid mixing and cooling, the streams may be mixed in certain embodiments using, for instance a venturi, spray tower or in the dehydrobromination reactor 1140 itself.

In product separation section 1150 one or more distillation columns are used to separate the compounds of dehydrobromination reactor discharge stream 1142 into propylene product stream 1156, HBr stream 1152, and bromopropane recycle stream 1154. In certain embodiments, the propylene may undergo a final water wash and a drying step in the product recovery section 1150. Propylene product stream 1156, may be high purity propylene, such as polymer grade propylene. HBr stream 1152 is predominantly HBr, and is fed to HBr oxidation 1160. Bromopropane stream 1154 is predominantly bromopropane and bromopropylene, and may include some HBr, dibromopropane, and propylene, and is recycled to the dehydrobromination reactor. In some embodiments, the distillations are carried out at a pressure high enough to allow for the use of cooling water in the condensers. In a certain embodiment, HBr is separated from propylene and bromopropane in the first distillation columns and propylene is separated from bromopropane in the second distillation column.

Bromopropane and bromopropylene have close boiling points and are difficult to separate using distillation. Consequently, small amounts of bromopropylene that are formed during bromination, hydrogenation and possibly dehydrobromination may accumulate in the bromopropane recycle loop, possibly resulting in an inoperable process or in the production of off-spec propylene product. Consequently, in certain embodiments, a fraction (0%-100%) of the bromopropane recycle stream 1154 is fed via stream 1158 to hydrobromination 1180, where the bromopropylene is reacted with HBr in the presence of a catalyst (e.g., WR Grace Silica Si1151) to form dibromopropane which is subsequently hydrogenated to bromopropane in 1130.

In the embodiment shown in FIG. 1A, oxidation feed streams 1152 and 1126 are mixed with oxygen, for instance through an air stream 1106. The HBr gas may then be oxidized over a catalyst, such as chromium or cerium oxide-based catalyst to produce bromine and water. The initiation temperature for this catalytic reaction is approximately 200° C., while the maximum stable operating temperature for the catalyst is approximately 700° C. HBr oxidation is a highly exothermic reaction and may be carried out using a reactor system, such as an isothermal reactor or a multiple stage adiabatic reactor system with intermediate cooling using quench and/or heat exchangers. Examples of such systems may be found in U.S. Pat. No. 7,883,568, issued Feb. 8, 2011, which is incorporated fully herein by reference.

In the embodiment shown in FIG. 1A, oxidation reactor exit stream 1162 is fed to bromine separator 1170. In bromine separator 170, the bromine in oxidation reactor exist stream 1162 may be subsequently condensed, and bromine and water (which are substantially immiscible) are separated, such as by using a decanter. Elemental bromine from bromine separator 1170 may be recycled to bromination reactor 1110 through bromine recycle stream 1172, while water and a gas stream (primarily including nitrogen and oxygen) may be discharged through water discharge stream 1174 and gas discharge stream 1176, respectively. In certain embodiments bromine recycle stream 1172 may be dried using a molecular sieve bed before it is recycled to bromination reactor 1110. In another embodiment bromine recycle stream 1172 may be dried using sulfuric acid distillation before it is recycled to bromination reactor 1110.

While the bulk of the bromine may be recovered by condensation in bromine separator 170, the gas stream, consisting primarily of nitrogen and the excess oxygen when air is used as the oxidizing stream, leaving the oxidation system may still contain a small amount of bromine. Cold (e.g., ~45° C.) aqueous sodium bromide may be used to recover the residual bromine using a reactive absorption process. The absorbed bromine may then be recovered using heterogeneous distillation, and the lean aqueous sodium bromide solution may be cooled and recycled to the absorber.

Feedstocks Other than Propane

As is understood by to one skilled in the art with the benefit of this disclosure, the present disclosure may be used for converting an alkane containing two or more carbon atoms, for example, ethane, n-butane, iso-butane and pentanes, to the corresponding olefin. As a non-limiting example, in certain embodiments of the present disclosure, process feedstream 102 of FIG. 1 or 1102 of FIG. 1A may be comprised of n-butane which is fed to bromination reactor 110 n-butane may be obtained from various sources, including conventional and unconventional hydrocarbon sources, or as a product of the manufacture of synthetic fuels (e.g. Fischer-Tropsch). n-butane is reacted with elemental bromine in bromination reactor 110 to produce bromobutane and HBr. In certain embodiments of the present disclosure, this reaction is not catalyzed, i.e., the reaction is thermally induced. In addition to bromobutane and HBr, the reaction forms byproducts dibromobutane, butyl polybromides, butylene, and other alkyl bromides. At higher temperatures, coke may also be formed in bromination reactor 110 of FIG. 1 or 1100 of FIG. 1A

The products of the reaction between n-butane and bromine formed in bromination reactor 110 and 1100 are the butyl analogs of those formed in the reaction between propane and bromine in bromination reactor 110 and 1100 shown in FIGS. 1 and 1A, respectively. Consequently, the sequence of steps employed in FIGS. 1 and 1A to form butene from bromobutane are the same as those described above, with high purity butane recovered from product line 172 and 1156, respectively.

EXAMPLES

Example 1

A half-inch glass tube reactor was used to conduct a series of bromination tests at various temperatures and product compositions, as shown in FIGS. 2A and 2B. Propane and bromine were added to the reactor, which was pre-heated to the desired temperature. The residence time for each test was 30 seconds. Data for each test was collected for 1 hour and the results averaged. Conversion to products based on propane was measured using GC analysis. Selectivity to bromopropane was measured by GC analysis. The results for each set of conditions are shown is FIGS. 2A and 2B.

Example 2

The reaction products of Example 1 for a bromine:propane molar ratio of 0.5 were sampled at 250° C. and 350° C. to determine the product composition. Results are shown in FIGS. 3A and 3B.

Example 3

An experiment was conducted to determine the results of dehydrobromination of 2-brompopropane to ethylene. The reaction was performed at 400° C. with a residence time of 1 second over a WR Grace Silica 1151 catalyst in a ½ in tube reactor. The reactant mixture was 50:50 nitrogen and bromoproane. The data was collected for one hour and the results averaged. The results are shown in FIG. 4.

Example 4

Example 3 was repeated at various temperatures as shown in FIG. 5 to compare experimental results to theoretical equilibrium results computed using Gibbs Free Energy minimization in Aspen Plus. The results of the comparison may be found FIG. 5.

Example 5

Figure 6:
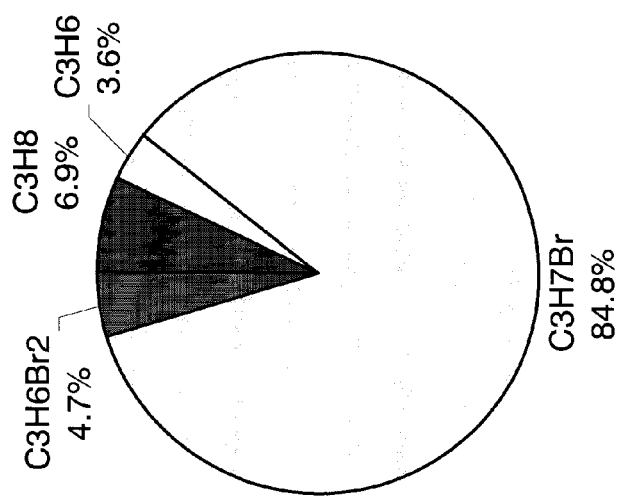
FIG. 6 is a graph showing the product distribution in mol % of hydrogenation of dibromopropane.

A sample of dibromopropane (DBP) was hydrogenated over a catalyst. The ratio of reactants ($H_2$/DBP/HBr) was 1:1:2. The catalyst was 1% Pd/$Al_2O_3$ (Alfa-Aesar 44820), the temperature was 200° C., and the residence time over the catalyst was 5 seconds. The resulting product distribution (in mol %) is shown in FIG. 6. Net bromopropane conversion was 87.5%.

In view of all of the above and the figures, one of ordinary skill in the art will readily recognize that the present disclosure introduces a process that includes brominating a $C_2$, $C_3$, $C_4$, $C_5$, or $C_6$ alkane with elemental bromine to form a bromoalkane, reacting the bromo-alkane to form a $C_2$, $C_3$ $C_4$, $C_5$ or $C_6$ alkene and HBr, and oxidizing the HBr to form elemental bromine.

The present disclosure also introduces a process wherein the alkane is ethane, propane, n-butane, isobutane, a pentane, or a hexane.

The present disclosure also introduces a process wherein the alkane is propane and the alkene is propylene.

In view of all of the above and the figures, one of ordinary skill in the art will readily recognize that the present disclosure further introduces a process that includes providing a feedstock comprising propane and reacting at least some of the propane with bromine to bromopropane and HBr. The bromopropane is dehydrobrominated to form a propylene/HBr mixture and the propylene/HBr mixture is separated to form propylene and recycle HBr. The process further includes oxidizing the HBr to form a bromine/water mixture, and separating bromine from the bromine/water mixture.

The present disclosure also introduces a process wherein the step of reacting at least some of the propane with bromine is thermally induced.

The present disclosure also introduces a process wherein the reaction occurs at a temperature of at least 200° C.

The present disclosure also introduces a process wherein the dehydrobrominating step takes place in the presence of a catalyst.

The present disclosure also introduces a process wherein the catalyst is selected from the group consisting of a silica-based catalyst, titanium dioxide, zirconium dioxide and their mixtures thereof.

The present disclosure also introduces a process wherein in the dehydrobrominating step, the bromopropane is heated to between 250° C. and 500° C.

The present disclosure also introduces a process wherein separating the propylene/HBr mixture is accomplished by distillation.

The present disclosure also introduces a process wherein separating the propylene/HBr mixture is accomplished by absorbing the HBr in aqueous HBr to form a concentrated HBr solution.

The present disclosure also introduces a process further includes after the step of absorbing the HBr in aqueous HBr to form a concentrated HBr solution stripping the HBr from the concentrated aqueous HBr;

The present disclosure also introduces a process wherein the HBr is oxidized using a chromium or cerium-based catalyst.

The present disclosure also introduces a process further including after the step of separating bromine from the bromine/water mixture recycling the bromine to react with the propane in the step of reacting at least some of the propane with bromine.

In view of all of the above and the figures, one of ordinary skill in the art will readily recognize that the present disclosure further introduces a process that includes providing a stream comprising primarily propane, reacting at least some of the propane with bromine to form a dibromopropane/bromopropane/HBr/propane mixture, and separating the dibromopropane, brompropane, HBr, and propane from the dibromopropane/bromopropane/HBr/propane mixture. The process also includes reacting the dibromopropane with hydrogen to form bromopropane, dehydrobrominating the bromopropane to form a propylene/HBr mixture, and separating the propylene/HBr mixture to form propylene and recycle HBr. In addition, the process includes oxidizing the recycle HBr to form a bromine/water mixture, and separating the bromine/water mixture to form recycle bromine.

The present disclosure also introduces a process wherein the step of reacting at least some of the propane with bromine is performed at a temperature of between 200° C. and 375° C.

The present disclosure also introduces a process wherein the step of reacting at least some of the propane with bromine is performed with a stoichiometric excess of propane.

The present disclosure also introduces a process wherein the step of reacting the dibromopropane with hydrogen is performed using a catalyst.

The present disclosure also introduces a process wherein the catalyst is Pd, Pt, Ni, Ru or Cu.

The present disclosure also introduces a process wherein the source of hydrogen is an alkane.

The present disclosure also introduces a process wherein the source of hydrogen is hydrogen.

The present disclosure also introduces a process wherein the hydrogen contains HBr.

The present disclosure also introduces a process wherein the dehydrobrominating step is performed using a catalyst, wherein the catalyst is selected from the group consisting of a silica-based catalyst, titanium dioxide, zirconium dioxide and their mixtures thereof.

The present disclosure also introduces a process wherein separating the propylene/HBr mixture is accomplished by absorbing the HBr in aqueous HBr to form a concentrated HBr solution.

The present disclosure also introduces a process that further includes after the step of absorbing the HBr in aqueous HBr to form a concentrated HBr solution stripping the HBr from the concentrated aqueous HBr;

The present disclosure also introduces a process wherein the step of oxidizing HBr is performed at a temperature of between 200° C. and 700° C.

The present disclosure also introduces a process wherein the step of separating the propylene/HBr mixture is accomplished by distillation.

In view of all of the above and the figures, one of ordinary skill in the art will readily recognize that the present disclosure also introduces a process that includes providing a process feed stream comprising primarily propane, reacting at least some of the propane in the process feed stream with bromine in a bromine recycle stream to form a dibromopropane/bromopropane/HBr/propane stream comprising a mixture of dibromopropane, bromopropane, HBr, and propane, and separating the dibromopropane/bromopropane/HBr/propane stream to form a dibromopropane stream, a bromopropane stream, a HBr stream, and a propane recycle stream. The process further includes combining the propane recycle stream with a fresh propane stream to form the process feed stream, and reacting the dibromopropane stream with a source of hydrogen. Further, the process includes combining the bromopropane stream with a portion of a bromopropane recycle stream to form a bromopropane feed stream, dehydrobrominating the bromopropane in the bromopropane feed stream to form a propylene/HBr/bromopropane mixture, and separating the propylene/HBr/bromopropane mixture to form a propylene product stream, a recycle HBr stream and the bromopropane recycle stream. The HBr stream and the recycle HBr stream are combined to form an oxidizer feed stream, the oxidizer feed stream is oxidized to form a bromine/water mixture stream, and the bromine/water mixture is separated to form recycle bromine stream.

The present disclosure also introduces a process that includes hydrobrominating at least a portion of the bromopropane recycle stream to form a mixture comprised of dibromopropane.

The present disclosure also introduces a process that further includes hydrogenating the dibromopropane mixture to form bromopropane.

In view of all of the above and the figures, one of ordinary skill in the art will readily recognize that the present disclosure also introduces a process that includes providing a process feed stream comprising propane, providing a bromine stream comprising bromine, and reacting at least some of the propane in the process feed stream with bromine in the bromine stream to form a dibromopropane/bromopropane/HBr/propane stream. The process also includes separating the dibromopropane/bromopropane/HBr/propane stream to form a lights stream comprising propane and HBr, a bromopropane stream, and a dibromopropane stream, combining the lights stream with aqueous HBr, and absorbing the HBr from the lights stream to form a recycle propane stream and a concentrated HBr stream. In addition, the process includes combining the recycle propane stream with a fresh propane stream to form the process feed stream, stripping dry HBr from the concentrated HBr stream to form a HBr gas stream, and combining the bromopropane stream with a recycle bromopropane stream to form a dehydrobromination feed stream. Further, the process includes dehydrobrominating the dehydrobromination feed stream to form a dehydrobromination reactor discharge stream comprising HBr, propylene, and bromopropane, absorbing the HBr in the dehydrobromination reactor discharge stream using aqueous HBr to form a propylene stream comprising primarily propylene and a concentrated HBr stripper feed stream, separating the bromopropane from the propylene, and stripping the HBr to form an HBr oxidation stream. Further, the process includes combining the HBr oxidation stream and the HBr gas stream to form an oxidation feed stream, oxidizing the oxidation feed stream to form a bromine/water mixture stream, and separating bromine from water in the bromine/water mixture stream to form the bromine stream.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes and structures for carrying out the same purposes and/or achieving the same advantages of the embodiments introduced herein. One of ordinary skill in the art should also realize that such equivalent constructions do not depart from the spirit and scope of the present disclosure, and that they may make various changes, substitutions and alterations herein without departing from the spirit and scope of the present disclosure.

What is claimed is:
1. A process comprising:
    brominating an alkane with elemental bromine to form a stream comprising bromo-alkane and dibromo-alkane, wherein the alkane is a $C_2$, $C_3$, $C_4$, $C_5$, or $C_6$ alkane;
    separating the dibromoalkane from the bromo-alkane,
    reacting the dibromoalkane, thermally or in the presence of a catalyst, with alkane to form additional bromo-alkane;

reacting the additional bromo-alkane to form a corresponding alkene of the alkane and HBr; and oxidizing the HBr to form elemental bromine.

2. The process of claim 1, wherein the alkane is ethane, propane, n-butane, isobutane, a pentane, or a hexane.

3. The process of claim 2, wherein the alkane is propane and the alkene is propylene.

4. A process comprising:
providing a feedstock comprising propane;
reacting at least some of the propane with bromine to form bromopropane, dibromopropane, and HBr;
separating the dibromopropane from the bromopropane,
reacting the dibromopropane, thermally or in the presence of a catalyst, with alkane to form additional bromopropane;
dehydrobrominating the additional bromopropane to form a propylene/HBrpropylene and HBr mixture;
separating the propylene/HBrpropylene and HBr mixture to form propylene and recycle HBr;
oxidizing the recycle HBr to form a bromine/waterbromine and water mixture;
and separating bromine from the bromine/waterbromine and water mixture.

5. The process of claim 4, wherein the step of reacting at least some of the propane with bromine is thermally induced.

6. The process of claim 5, wherein the reaction occurs at a temperature of at least 200° C.

7. The process of claim 4, wherein the dehydrobrominating step takes place in the presence of a catalyst.

8. The process of claim 7, wherein the catalyst is selected from the group consisting of a silica-based catalyst, titanium dioxide, zirconium dioxide and their mixtures thereof.

9. The process of claim 7, wherein in the dehydrobrominating step, the bromopropane is heated to between 250° C. and 500° C.

10. The process of claim 4, wherein separating the propylene and HBr mixture is accomplished by distillation.

11. The process of claim 4, wherein separating the propylene and HBr mixture is accomplished by absorbing the HBr in aqueous HBr to form a concentrated HBr solution.

12. The process of claim 11, further comprising after the step of absorbing the HBr in aqueous HBr to form a concentrated HBr solution:
stripping the HBr from the concentrated aqueous HBr.

13. The process of claim 4, wherein the HBr is oxidized using a chromium or cerium-based catalyst.

14. The process of claim 4, further comprising after the step of separating bromine from the propylene and HBr mixture:
recycling the bromine to react with the propane in the step of reacting at least some of the propane with bromine.

15. The process of claim 1, wherein the alkane is propane, the bromo-alkane is bromopropane, the dibromo-alkane is dibromopropane, and the alkene is propylene, and wherein the process further comprises converting the dibromopropane directly to propylene using Zn, wherein $ZnBr_2$ is produced as a byproduct.

16. The process of claim 15, further comprising using oxidation or electrolysis and the $ZnBr_2$ to regenerate $Br_2$.

17. A process comprising:
brominating an alkane with elemental bromine in a bromination reactor to form a stream comprising bromo-alkane and dibromo-alkane, wherein the alkane is a C2, C3, C4, C5 or C6 alkane;
separating the dibromoalkane from the bromo-alkane,
reacting the dibromoalkane, thermally or in the presence of a catalyst, with alkane to form additional bromo-alkane;
reacting the additional bromo-alkane to form a corresponding alkene of the alkane and HBr;
and oxidizing the HBr to form elemental bromine.

18. The process of claim 17, wherein the dibromo-alkane is recycled to the bromination reactor for the reacting of the dibromo-alkane with the alkane to form bromo-alkane.

19. The process of claim 17, wherein the reacting of the dibromo-alkane with the alkane to form bromo-alkane occurs in a separate reactor from the bromination reactor.

* * * * *